United States Patent [19]

Best et al.

[11] Patent Number: 5,430,954
[45] Date of Patent: Jul. 11, 1995

[54] MEASURING CALLIPER

[75] Inventors: Robert E. Best, London; Gordon A. Lawrence, Barnet, both of United Kingdom; Fredrick G. DeGrave, Gooweg, Netherlands

[73] Assignee: Robert Pringle Engineers Limited, London, United Kingdom

[21] Appl. No.: 15,652

[22] Filed: Feb. 9, 1993

[30] Foreign Application Priority Data

Feb. 25, 1992 [GB] United Kingdom ............... 9203945
Sep. 18, 1992 [GB] United Kingdom ............... 9219817

[51] Int. Cl.6 .............................................. G01B 5/06
[52] U.S. Cl. ............................................. 33/793; 33/784; 33/797
[58] Field of Search ............... 33/798, 793, 797, 800, 33/801, 802, 794, 807, 784, 815

[56] References Cited

U.S. PATENT DOCUMENTS

| | | | |
|---|---|---|---|
| 2,421,517 | 6/1947 | Moerman | 33/797 |
| 2,768,446 | 10/1956 | Gorr | 33/798 |
| 2,785,471 | 3/1957 | Aldeborgh et al. | 33/800 |
| 4,034,477 | 7/1977 | Von Voros | 33/794 |
| 4,315,472 | 2/1982 | Kinkead | 33/798 |
| 4,345,380 | 8/1982 | Vis | 33/793 |
| 4,599,800 | 7/1986 | Wyrwich et al. | 33/512 |
| 4,612,656 | 9/1986 | Suzuki et al. | 33/784 |
| 4,845,646 | 7/1989 | Marquis et al. | 33/784 |
| 5,029,402 | 7/1991 | Lazecki et al. | 33/784 |
| 5,074,051 | 12/1991 | Cordy et al. | 33/797 |

Primary Examiner—Thomas B. Will
Attorney, Agent, or Firm—Michael Y. Epstein

[57] ABSTRACT

There is disclosed a calliper, useful for measuring how much fat can be pinched beneath the skin, having jaws (4,6) pivotally mounted for relative pivotal movement. The movement is amplified by a gear train (24, 26, 28, and 30). The final gear wheel (30) drives a toothed wheel the movement of which is sensed by an opto sensor (34). A digital readout indicates the spacing between the jaws for indicating the spacing between measuring surfaces of the jaws. In contrast to conventional callipers, which are used only to transfer a dimension from an object to be measured to a measuring device, the callipers disclosed give a direct reading of the spacing between the measuring surfaces.

5 Claims, 4 Drawing Sheets

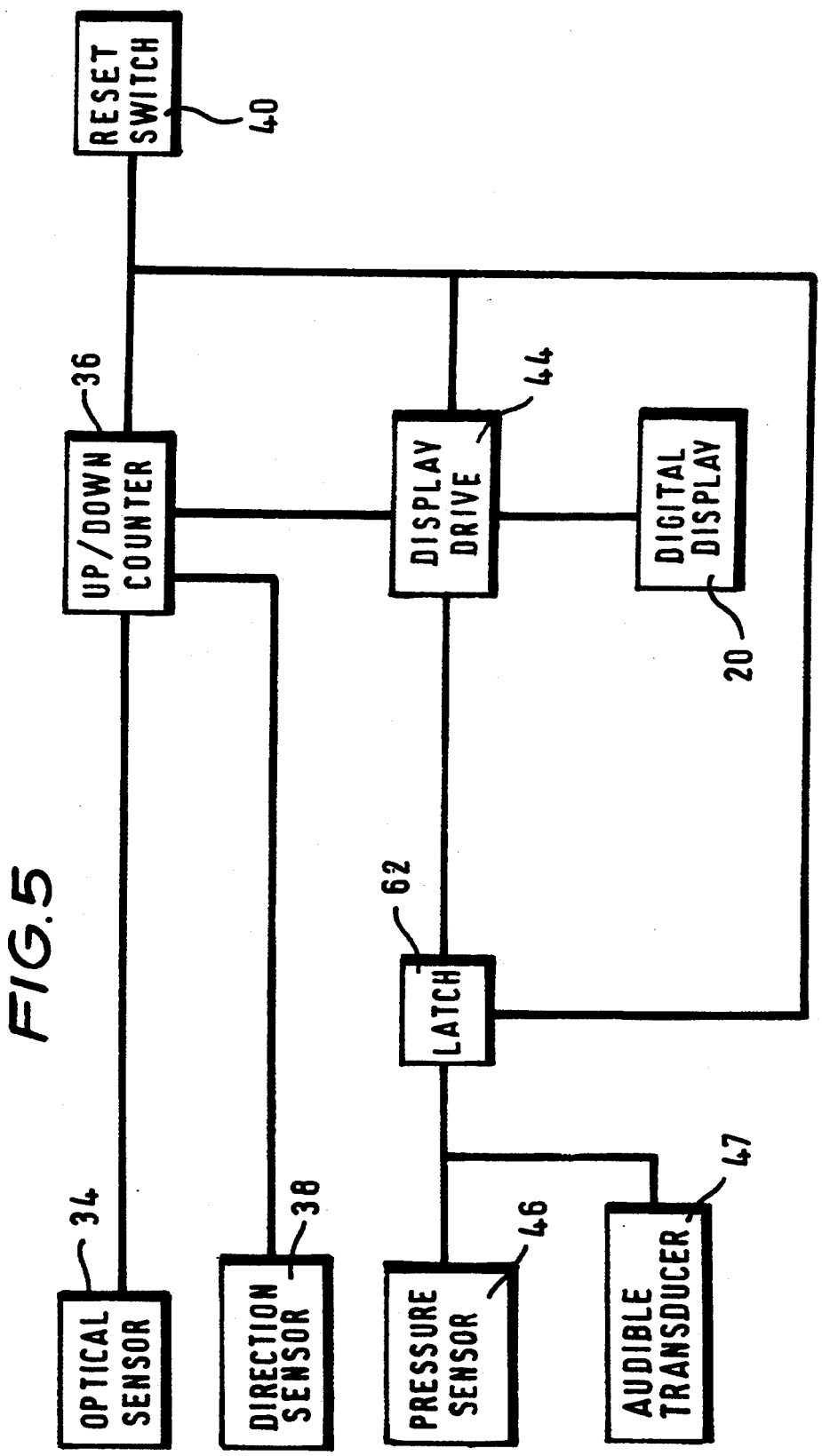

in the image in FIG. 1. so that the outer

MEASURING CALLIPER

BACKGROUND OF THE INVENTION

This invention relates to measuring callipers.

The background of the invention will be described with reference to an application related to personal health and fitness. It will be appreciated, however, that the invention is applicable in other fields and many other applications will doubtless occur to the reader.

One way of determining whether a person is overweight and, if so, by how much, is to see how much fat can be pinched beneath the skin. A much publicized rule of thumb is that you are overweight if you can pinch more than an inch. Determining just how much fat you can pinch is not very easy, however. If you wanted to measure it, you would have to pinch the relevant area between finger and thumb, to remove said finger and thumb from the area whilst holding them steady, and then measure the distance between them. That is not likely to lead to an accurate assessment.

SUMMARY OF THE INVENTION

In accordance with the invention, there is provided a calliper comprising jaws pivotally mounted for relative pivotal movement; said jaws having opposed measuring surfaces; and means responsive to said movement for indicating the spacing between measuring surfaces of the jaws. In contrast to conventional callipers, which are used only to transfer a dimension from an object to be measured to a measuring device, callipers in accordance with the invention give a direct reading of the spacing between the measuring surfaces and thus, in the envisaged application, of the thickness of fat which can be "pinched".

In a preferred arrangement, the means for indicating includes a position representative member having sensible means, a sensor for sensing the sensible means at a predetermined position, the position representative member and the sensor being arranged for relative movement with the relative movement between the jaws, and means for accumulating a total of the times the sensible means is sensed at the predetermined position during movement from an initial position.

In the preferred arrangement, the means for accumulating preferably includes means for sensing the direction of relative movement of the jaws to add to the total, when the jaws are moving in one relative direction, and to subtract from the total, when the jaws are moving in the opposite direction.

Most preferably, the position representative member is a wheel driven to rotate from relative pivotal movement between the jaws by a gear train. By this means the movement of the jaws can produce a greater movement in the position representative wheel. Thus, finer resolution can be provided in the indication of position, than would be possible given the same spacing of the sensible features if these were provided directly on a jaw. Generally there will be a plurality of sensible features equally spaced around the wheel. In an extreme case, there will be only one feature so that the sensor senses the feature once in each revolution of the wheel.

Preferably, the means for sensing the direction of relative movement includes a switch member biassed into frictional engagement with the wheel and mounted for movement by said frictional engagement to make electrical contact with a contact member when the wheel rotates in one direction, and to break contact with the contact member when the wheel rotates in the other direction.

In order to contain the gear train sensors and means for indicating etc., the calliper preferably has a hollow body member in which they can be housed. Especially in this case, but also more generally, the gear train preferably includes mutually meshed gearwheels each mounted for movement with a respective jaw about its pivotal axis, one of the mutually meshed gears also being arranged to drive the position representative wheel member directly or through one or more other gears.

The sensible features may be in any convenient form compatible with the sensor, e.g. magnetic features sensible by, say, a reed switch, or mechanical protuberances sensible by a microswitch. In one convenient form, the position representative wheel member has a plurality of features which may be sensed optically, and the means for sensing the features comprises an optosensor. The optically sensible features may, for example, be holes through an opaque wheel, opaque marks on a transparent wheel, or, in a preferred form, teeth on an opaque wheel.

In order to allow the callipers to be operated conveniently with one hand, means is preferably provided to bias the jaws resiliently towards each other and lever means attached to each jaw by which they may be opened.

In order to provide consistent results with the minimum amount of skill on the part of the user, the callipers preferably include a pressure sensitive switch mounted in one jaw so as to operate when the measuring surfaces of the jaws exert a predetermined pressure on the object to be measured; and means to latch the spacing indicated by the means for indicating, on operation of the switch.

DESCRIPTION OF THE DRAWINGS

One embodiment of the invention will now be described, by way of example, with reference to the accompanying drawings, in which:

FIG. 5 is a block diagram of the electrical circuit of the callipers of FIG. 1.

DESCRIPTION OF PREFERRED EMBODIMENTS

Figure 1:
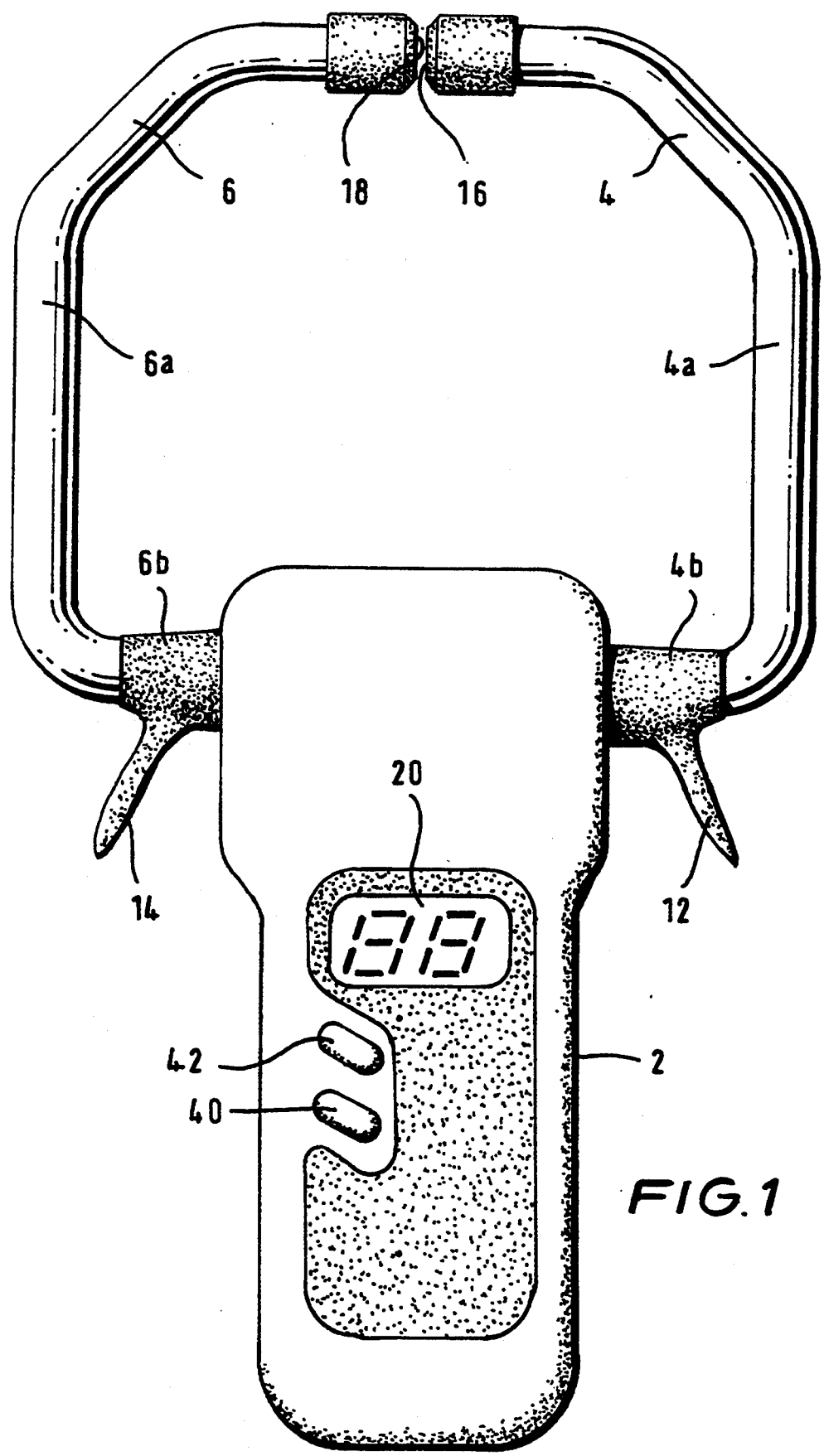
FIG. 1 is a front view of callipers embodying the invention.
Figure 2:
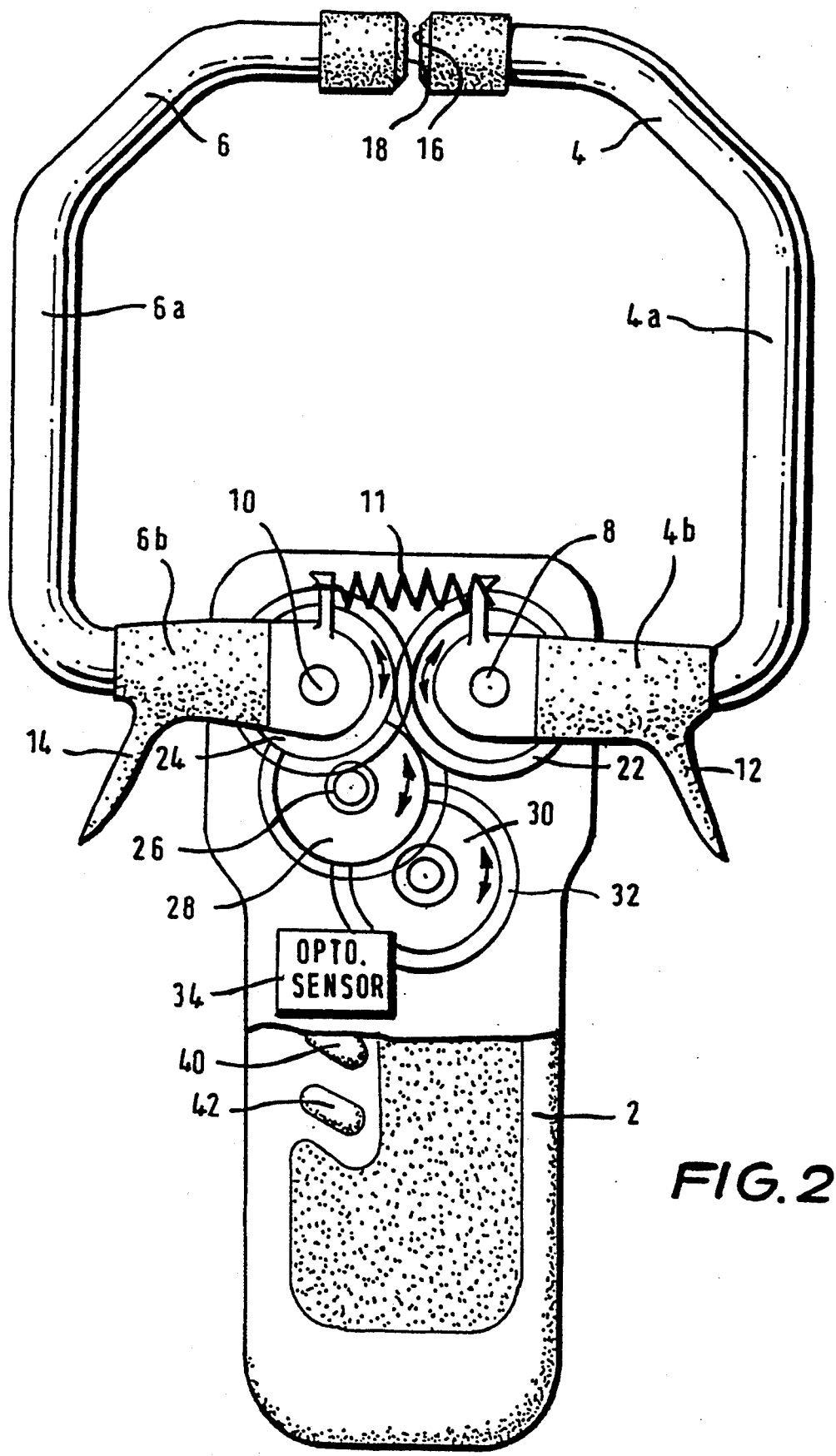
FIG. 2 is a broken view of the callipers of FIG. 1, showing its gear train.

Referring to the drawings, measuring callipers have a hollow body 2 from which opposed jaws 4 and 6 extend. The jaws 4 and 6 are mounted in the body on shafts 8 and 10 for pivotal movement relative to the body and to each other. The jaws are resiliently biased towards each other by a spring 11. Levers 12 and 14, project from the jaws so that they may be opened against the bias of the spring by squeezing the levers together. A preferred feature of the arrangement illustrated, is that the jaws are formed in two parts 4a, 4b and 6a, 6b. The outer part 4a, 6a of each jaw is pivotally mounted on the inner part 4b, 6b for movement about an axis transverse to the page in FIG. 1, so that the outer parts 4a and 6a can be folded down over the body 2 so reducing the overall size of the device. Each inner jaw part 4b, 6b is moulded integrally in a plastics material with its associated lever 12,14.

In use, the jaws are opened by squeezing the levers 12 and 14 and placed around the object which it is desired to measure. In the envisaged health monitoring use, that would be a pinch of fat, say, on the user's abdomen. The pressure on the levers is then relaxed so that the spring closes measuring surfaces 16 and 18 at the tips of the jaws on the object.

In order to read the measurement directly, in contrast to the traditional way of using callipers in which the measurement is transferred to a rule for example, the callipers illustrated include means responsive to relative movement between the jaws for driving a digital display in the form of an LED display 20 to indicate the spacing between the measuring surfaces 16 and 18.

To this end, mounted on each shaft 8 and 10 for movement with the respective jaw, is a respective gearwheel 22 and 24. Although complete gearwheels are shown that is not entirely necessary since the rotation of the shafts and the jaws is restricted to pivotal movement which does not involve a complete revolution. The gear wheels 22 and 24 mesh with each other so that movement of one jaw relative to the body (not shown in FIG. 3) produces an equal but opposite movement of the other jaw relative to the body.

The gears are part of a gear train which also includes gears 26, 28, and 30 arranged to drive a toothed wheel 32 faster than the rate at which the jaws and thus the gear wheels 22 and 24 rotate.

The teeth of the wheel 32 run between the light source and the detector of an optosensor 34. As the teeth pass between the detector and the light source of the optosensor, they interrupt the light so producing a pulse in the output of the detector. Counting the number of pules during movement of the jaws from an initial position, e.g. closed, represents the distance between their measuring surfaces 16 and 18.

The block diagram of a circuit for counting the pulses produced by the optosensor 34 is shown in FIG. 5. The output of the optosensor is received by a first input of an up/down counter 36. So that the counter will accommodate the jaws being opened and then closed onto the object to be measured, a direction sensor 38, which is sensitive to whether the jaws are opening or closing, provides an input signal to a second input of the up/down counter, to control whether it counts up or down.

The counter is initially reset to zero by a reset switch 40 or by switching the apparatus on at a switch 42. Squeezing the levers 12 and 14 together pivots the jaws about their shafts 8 and 10 so driving the wheel 32 to rotate via the gear train. The direction of rotation is sensed as opening and the pulses produced by the optosensor 34 are accumulated representing at each stage the distance between the measuring surfaces of the jaws. As the pressure on the levers 12 and 14 is relaxed to allow the jaws to close on the object to be measured, the direction of movement of the jaws is sensed by the direction sensor 38 to be closing, which provides a signal indicative of the change of direction to the counter 36 which therefore subtracts the following pulses from the count already accumulated. The counter will thus count up and down alternately each time the direction is reversed. In practice, there would normally be at least one reverse of direction in the envisaged application for measuring a pinch of fat.

The output of the up/down counter is fed to a display driver 44. Once the jaws have closed on the object to be measured under the action of the spring, the spacing between the measuring surfaces 16 and 18 may be read from the display 20 which may be calibrated in any desired units either by adjusting the gear ratio and spacing of the teeth on the wheel 32 in relation to the distance of the measuring surfaces 16 and 18 from the axes of the respective shafts 8 and 10, or by interposing a unit (not shown) to translate the output of the counter 36 into some other number, or by a combination of both.

Since it may be a little inconvenient to have to read the display whilst the measurement is being made, the output of the display driver may be latched.

Figure 3:
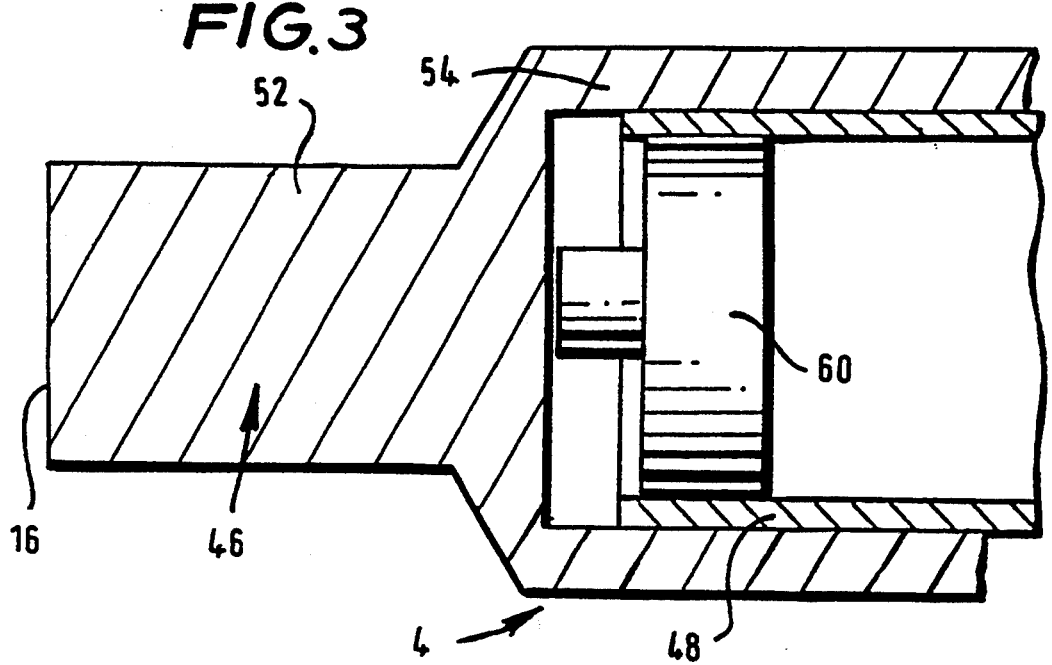
FIG. 3 is a sectional detail of the tip of one of the jaws showing a pressure sensitive switch.

In order also to increase the repeatability of the readings, one of the measuring surfaces (illustrated as surface 16 in the jaw 4) contains a pressure sensitive switch 46 illustrated in section in FIG. 3. The jaw 4 is in the form of a hollow tube 48 the free end of which has a resilient boot 52 e.g. of synthetic rubber. The boot comprises a solid button the outer end of which constitutes the measuring surface 16 and a hollow cylindrical portion 54 which fits over the end of the tube 48. Behind the boot 52 a microswitch 60 is mounted in the end of the tube 48. As will be appreciated, sufficient pressure on the measuring surface 16 of the button deforms the boot to operate the microswitch 60. The microswitch operates at a predetermined pressure which is determined by the force necessary to operate it and the area of the surface 16. The microswitch 60 is connected to a latch 62 which, once the switch has operated, provides a latched output to the display driver 44 so freezing the output thereof until reset by operation of the on/off switch 42 or the reset switch 40. Operation of the latch may be indicated to the user by a sounder 47 triggered by the operation of the microswitch 60 to emit an audible "beep".

Figure 4:
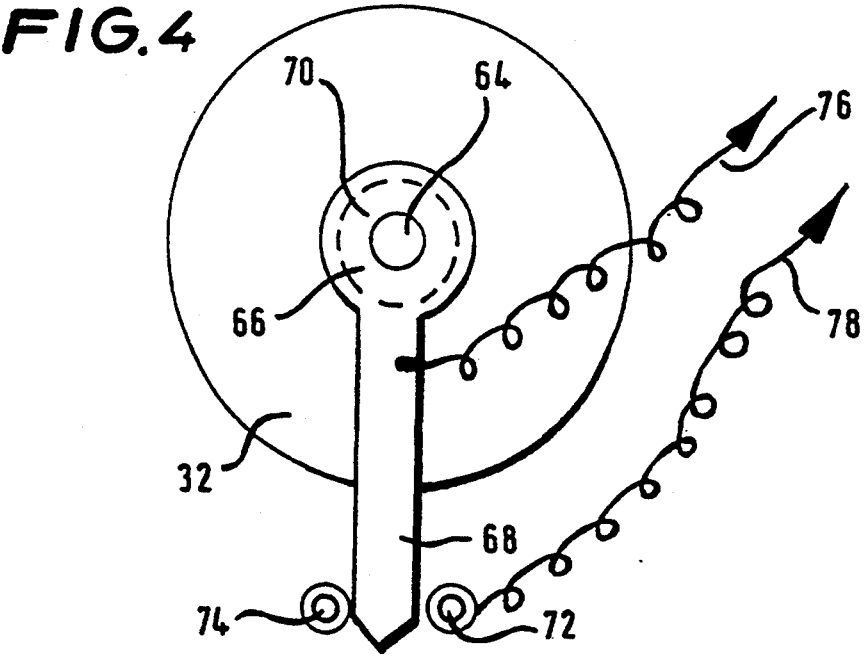
FIG. 4 is a schematic detail showing a direction sensor.

An example of a direction sensing device is shown in FIG. 4. The toothed wheel 32 is mounted for rotation on a shaft 64. A switch member in the form of an arm 68 has a boss 66 at one end. The boss receives the shaft so that the wheel 32 can rotate relative to the arm. A nylon washer 70 is biassed by means (not shown) into contact with the boss 66 to urge the boss into frictional engagement with the wheel 32. As the wheel rotates, the arm 68 is thus urged by friction to rotate in the same direction. Two contacts in the form of posts 72 and 74 are mounted close together and on opposite sides of the arm 68 so that clockwise movement of the arm 68 is arrested by the post 74 and anticlockwise movement is arrested by the post 72. The arm 68 and the post 72 are electrically conducting, e.g. formed of gold plated brass, and are connected by leads 76 and 78 between a voltage reference (not shown) and the second input of the up/down counter. When the jaws 4 and 6 are opening, the wheel 32 rotates anti-clockwise bringing the arm 68 into electrical contact with the post 72 and so connecting the voltage reference to the second input of the up/down counter 36 causing it to add pulses from the optical sensor 34 to the total.

We claim:

1. A caliper comprising: jaws pivotally mounted for relative pivotal movement; said jaws having opposed measuring surfaces; means responsive to said movement for indicating the spacing between said measuring surfaces of the jaws, said indicating means including a position representative member having a sensible means: a sensor for sensing the sensible means at a predetermined position, the position representative member and the sensor being arranged for relative movement with the relative movement between the jaws; and means for accumulating a total of the times the sensible means is sensed at the predetermined position during movement from an initial position of the jaws, said accumulating means including means for sensing the direction of relative movement of the jaws to add to the total, when the jaws are moving in one relative direction, and to subtract from the total, when the jaws are moving in the opposite direction; said position representative member being a wheel driven to rotate from relative pivotal movement between the jaws by a gear train; and said means for sensing the direction of relative movement including a switch member biased into frictional engagement with the wheel and mounted for movement by said frictional engagement to make electrical contact with a contact member when the wheel rotates in one direction, and to break contact with the contact member when the wheel rotates in the other direction.

2. A calliper as claimed in claim 1, wherein the sensible means comprises a plurality of features each of which is sensed optically, and wherein the means for sensing the features comprises an optosensor.

3. A calliper as claimed in claim 2, wherein the features are teeth.

4. A caliper comprising: jaws pivotally mounted for relative pivotal movement; said jaws having opposed measuring surfaces; means responsive to said movement for indicating the spacing between said measuring surfaces of the jaws; a pressure sensitive switch mounted in one jaw so as to operate when the measuring surfaces of the jaws exert a predetermined pressure on an object to be measured; means to latch the spacing indicated by the means for indicating, on operation of the switch; said spacing indicating means being included in an electrical circuit comprising a display device for displaying a varying image representation of the varying spacing between said measuring surfaces during movement of said jaws, a drive means responsive to said jaw movement for controlling said display device, said latch means latching operation of said drive means for latching the image then being shown upon operation of said switch and independently of further movement of said jaws; one of said jaws including, adjacent to the measuring surface thereof, an open-ended, hollow tube, said pressure sensitive switch being fixedly mounted in said tube adjacent to said open end, and a boot of a resilient material mounted on said tube, said boot having a first surface operatively associated with said switch and a second surface oppositely disposed to said first surface and comprising said measuring surface of said one jaw, whereby, upon contacting of said second surface with an object being measured by said caliper, contacting pressure is transmitted through said boot to said switch via said first surface.

5. A caliper comprising: jaws pivotally mounted for relative pivotal movement; said jaws having opposed measuring surfaces; means responsive to said movement for indicating the spacing between said measuring surfaces of the jaws; a pressure sensitive switch mounted in one jaw so as to operate when the measuring surfaces of the jaws exert a predetermined pressure on an object to be measured; means to latch the spacing indicated by the means for indicating, on operation of the switch; one of said jaws including, adjacent to the measuring surface thereof, an open-ended, hollow tube, said pressure sensitive switch being fixedly mounted in said tube adjacent to said open end, and a boot of a resilient material mounted on said tube, said boot having a first surface operatively associated with said switch and a second surface oppositely disposed to said first surface and comprising said measuring surface of said one jaw, whereby, upon contacting of said second surface with an object being measured by said caliper, contacting pressure is transmitted through said boot to said switch via said first surface.

* * * * *